(12) United States Patent
Seguin

(10) Patent No.: US 11,504,234 B2
(45) Date of Patent: Nov. 22, 2022

(54) CARDIAC VALVE REPAIR SYSTEM AND METHODS OF USE

(71) Applicant: BMEYE B.V., Irvine, CA (US)

(72) Inventor: Jacques Seguin, Gstaad (CH)

(73) Assignee: BMEYE B.V., Irvine, CA (US)

( * ) Notice: Subject to any disclaimer, the term of this patent is extended or adjusted under 35 U.S.C. 154(b) by 94 days.

(21) Appl. No.: 16/993,458

(22) Filed: Aug. 14, 2020

(65) Prior Publication Data

US 2020/0368020 A1 Nov. 26, 2020

Related U.S. Application Data

(60) Continuation of application No. 16/146,073, filed on Sep. 28, 2018, now Pat. No. 10,743,988, which is a division of application No. 15/494,107, filed on Apr. 21, 2017, now Pat. No. 10,383,724, which is a continuation of application No. 14/188,442, filed on Feb. 24, 2014, now Pat. No. 9,629,716, which is a
(Continued)

(51) Int. Cl.
*A61F 2/24* (2006.01)

(52) U.S. Cl.
CPC ............ *A61F 2/2427* (2013.01); *A61F 2/243* (2013.01); *A61F 2/2409* (2013.01); *A61F 2/2436* (2013.01); *A61F 2/2442* (2013.01); *A61F 2/24* (2013.01); *A61F 2/2412* (2013.01); *A61F 2/2418* (2013.01); *A61F 2/2433* (2013.01); *A61F 2210/0014* (2013.01); *A61F 2220/0016* (2013.01); *A61F 2220/0025* (2013.01); *A61F 2220/0033* (2013.01); *A61F 2230/001* (2013.01); *A61F 2230/0006* (2013.01); *A61F 2230/0013* (2013.01); *A61F 2230/0091* (2013.01); *A61F 2250/006* (2013.01); *A61F 2250/0039* (2013.01); *A61F 2250/0069* (2013.01); *A61F 2250/0098* (2013.01)

(58) Field of Classification Search
CPC .................................................... A61F 2/2409
See application file for complete search history.

(56) References Cited

U.S. PATENT DOCUMENTS

| 4,035,849 A | 7/1977 | Angell et al. |
| 4,490,859 A | 1/1985 | Black et al. |
| 4,512,338 A | 4/1985 | Balko et al. |

(Continued)

FOREIGN PATENT DOCUMENTS

| DE | 19532846 A1 | 3/1997 |
| DE | 19907646 A1 | 8/2000 |

(Continued)

OTHER PUBLICATIONS

Kempfert et al., "Minimally Invasive Off-Pump Valve-in-a-Ring Implantation: The Atrial Transcatheter Approach for Re-Operative Mitral Valve Replacement After Failed Repair", European Journal of Cardio-Thoracic Surgery, 2009, 35, pp. 965-969.

*Primary Examiner* — Rebecca S Preston
(74) *Attorney, Agent, or Firm* — Edwards Lifesciences

(57) ABSTRACT

Systems and methods for mitral valve repair having a docking station and a valve implant. The docking station is an anchoring device having a helix structure. The valve implant is made of an expandable frame and a valve, and is radially expandable to a diameter that is at least the same as an expanded diameter of the anchoring device. The method of delivering the docking station and valve implant is performed by inserting the components through device delivery catheters.

9 Claims, 6 Drawing Sheets

Related U.S. Application Data division of application No. 12/839,363, filed on Jul. 19, 2010, now Pat. No. 8,657,872.

(56) References Cited

U.S. PATENT DOCUMENTS

| | | | |
|---|---|---|---|
| 4,790,843 A | 12/1988 | Carpentier et al. | |
| 5,059,177 A | 10/1991 | Towne | |
| 5,156,621 A | 10/1992 | Navia et al. | |
| 5,403,305 A | 4/1995 | Sauter et al. | |
| 5,411,552 A | 5/1995 | Andersen et al. | |
| 5,443,500 A | 8/1995 | Sigwart | |
| 5,554,185 A | 9/1996 | Block et al. | |
| 5,840,081 A | 11/1998 | Andersen et al. | |
| 6,120,534 A | 9/2000 | Ruiz | |
| 6,168,614 B1 | 1/2001 | Andersen et al. | |
| 6,235,042 B1 | 5/2001 | Katzman | |
| 6,306,141 B1 | 10/2001 | Jervis | |
| 6,406,492 B1 | 6/2002 | Lytle | |
| 6,409,758 B2 | 6/2002 | Stobie et al. | |
| 6,419,696 B1 | 7/2002 | Ortiz et al. | |
| 6,425,916 B1 | 7/2002 | Garrison et al. | |
| 6,432,134 B1 | 8/2002 | Anson et al. | |
| 6,458,153 B1 | 10/2002 | Bailey et al. | |
| 6,527,979 B2 | 3/2003 | Constantz et al. | |
| 6,582,462 B1 | 6/2003 | Andersen et al. | |
| 6,652,578 B2 | 11/2003 | Bailey et al. | |
| 6,730,121 B2 | 5/2004 | Ortiz et al. | |
| 6,797,002 B2 | 9/2004 | Spence et al. | |
| 6,908,481 B2 | 6/2005 | Cribier | |
| 7,018,408 B2 | 3/2006 | Bailey et al. | |
| 7,037,334 B1 | 5/2006 | Hlavka et al. | |
| 7,077,861 B2 | 7/2006 | Spence | |
| 7,101,395 B2 | 9/2006 | Tremulis et al. | |
| 7,125,421 B2 | 10/2006 | Tremulis et al. | |
| 7,166,126 B2 | 1/2007 | Spence et al. | |
| 7,166,127 B2 | 1/2007 | Spence et al. | |
| 7,404,824 B1 | 7/2008 | Webler et al. | |
| 7,431,726 B2 | 10/2008 | Spence et al. | |
| 7,445,632 B2 | 11/2008 | McGuckin, Jr. et al. | |
| 7,585,321 B2 | 9/2009 | Cribier | |
| 7,618,446 B2 | 11/2009 | Andersen et al. | |
| 7,637,946 B2 | 12/2009 | Solem et al. | |
| 7,708,775 B2 | 5/2010 | Rowe et al. | |
| 7,737,060 B2 | 6/2010 | Strickler et al. | |
| 7,785,366 B2 | 8/2010 | Maurer et al. | |
| 7,951,195 B2 | 5/2011 | Antonsson et al. | |
| 8,142,492 B2 | 3/2012 | Forster et al. | |
| 8,236,049 B2 | 8/2012 | Rowe et al. | |
| 8,323,335 B2 | 12/2012 | Rowe et al. | |
| 8,377,115 B2 | 2/2013 | Thompson | |
| 8,398,708 B2 | 3/2013 | Meiri et al. | |
| 8,449,605 B2 | 5/2013 | Lichtenstein et al. | |
| 8,449,606 B2 | 5/2013 | Eliasen et al. | |
| 8,657,872 B2 | 2/2014 | Seguin | |
| 8,663,322 B2 | 3/2014 | Keranen | |
| 8,672,998 B2 | 3/2014 | Lichtenstein et al. | |
| 8,685,086 B2 | 4/2014 | Navia et al. | |
| 8,734,507 B2 | 5/2014 | Keranen | |
| 8,801,776 B2 | 8/2014 | House et al. | |
| 9,078,747 B2 | 7/2015 | Conklin | |
| 9,095,434 B2 | 8/2015 | Rowe | |
| 9,119,718 B2 | 9/2015 | Keranen | |
| 9,192,471 B2 | 11/2015 | Bolling | |
| 9,237,886 B2 | 1/2016 | Seguin et al. | |
| 9,314,335 B2 | 4/2016 | Konno | |
| 9,364,326 B2 | 6/2016 | Yaron | |
| 9,463,268 B2 | 10/2016 | Spence | |
| 9,474,599 B2 | 10/2016 | Keranen | |
| 9,597,205 B2 | 3/2017 | Tuval | |
| 9,622,863 B2 | 4/2017 | Karapetian et al. | |
| 2002/0032481 A1 | 3/2002 | Gabbay | |
| 2002/0045936 A1 | 4/2002 | Moe | |
| 2002/0107535 A1 | 8/2002 | Wei et al. | |
| 2002/0151970 A1 | 10/2002 | Garrison et al. | |
| 2002/0173841 A1 | 11/2002 | Ortiz et al. | |
| 2003/0167089 A1 | 9/2003 | Lane | |
| 2003/0225420 A1 | 12/2003 | Wardle | |
| 2004/0049207 A1 | 3/2004 | Goldfarb et al. | |
| 2004/0111006 A1 | 6/2004 | Alferness et al. | |
| 2004/0260389 A1 | 12/2004 | Case et al. | |
| 2005/0096736 A1 | 5/2005 | Osse et al. | |
| 2005/0119682 A1 | 6/2005 | Nguyen et al. | |
| 2005/0119735 A1 | 6/2005 | Spence et al. | |
| 2005/0137691 A1 | 6/2005 | Salahieh et al. | |
| 2005/0182486 A1 | 8/2005 | Gabbay | |
| 2005/0203614 A1 | 9/2005 | Forster et al. | |
| 2005/0203617 A1 | 9/2005 | Forster et al. | |
| 2006/0025857 A1 | 2/2006 | Bergheim et al. | |
| 2006/0195134 A1 | 8/2006 | Crittenden | |
| 2006/0265056 A1 | 11/2006 | Nguyen et al. | |
| 2007/0162103 A1 | 7/2007 | Case et al. | |
| 2007/0203575 A1 | 8/2007 | Forster et al. | |
| 2007/0265700 A1 | 11/2007 | Eliasen et al. | |
| 2007/0293808 A1 | 12/2007 | Williams et al. | |
| 2008/0033542 A1 | 2/2008 | Antonsson et al. | |
| 2008/0077235 A1 | 3/2008 | Kirson | |
| 2008/0109075 A1 | 5/2008 | Keranen | |
| 2008/0125853 A1 | 5/2008 | Bailey et al. | |
| 2008/0208330 A1 | 8/2008 | Keranen | |
| 2008/0228265 A1 | 9/2008 | Spence et al. | |
| 2008/0275503 A1 | 11/2008 | Spence et al. | |
| 2009/0177278 A1 | 7/2009 | Spence | |
| 2009/0192601 A1 | 7/2009 | Rafiee et al. | |
| 2009/0259307 A1 | 10/2009 | Gross et al. | |
| 2009/0299471 A1 | 12/2009 | Keranen | |
| 2009/0319037 A1 | 12/2009 | Rowe et al. | |
| 2010/0036484 A1 | 2/2010 | Hariton et al. | |
| 2010/0076549 A1 | 3/2010 | Keidar et al. | |
| 2010/0145440 A1 | 6/2010 | Keranen | |
| 2010/0161047 A1 | 6/2010 | Cabiri | |
| 2010/0312333 A1 | 12/2010 | Navia et al. | |
| 2010/0318184 A1 | 12/2010 | Spence | |
| 2010/0331971 A1 | 12/2010 | Keranen et al. | |
| 2011/0098802 A1 | 4/2011 | Braido et al. | |
| 2012/0059458 A1 | 3/2012 | Buchbinder et al. | |
| 2012/0123529 A1 | 5/2012 | Levi et al. | |
| 2012/0283820 A1 | 11/2012 | Tseng et al. | |
| 2013/0190865 A1 | 7/2013 | Anderson | |
| 2014/0074299 A1 | 3/2014 | Endou et al. | |
| 2014/0081394 A1 | 3/2014 | Keranen et al. | |
| 2014/0172070 A1 | 6/2014 | Seguin | |
| 2014/0358222 A1 | 12/2014 | Gorman, III et al. | |
| 2014/0379074 A1 | 12/2014 | Spence et al. | |
| 2015/0025623 A1 | 1/2015 | Granada et al. | |
| 2015/0230921 A1 | 8/2015 | Chau et al. | |
| 2015/0245910 A1 | 9/2015 | Righini et al. | |
| 2015/0282931 A1 | 10/2015 | Brunnett et al. | |
| 2015/0335428 A1 | 11/2015 | Keranen | |
| 2015/0335430 A1 | 11/2015 | Loulmet et al. | |
| 2015/0374493 A1 | 12/2015 | Yaron et al. | |
| 2016/0015514 A1 | 1/2016 | Lashinski et al. | |
| 2016/0074165 A1 | 3/2016 | Spence et al. | |
| 2016/0095705 A1 | 4/2016 | Keranen et al. | |
| 2016/0143732 A1 | 5/2016 | Glimsdale | |
| 2016/0184095 A1 | 6/2016 | Spence et al. | |
| 2016/0199177 A1 | 7/2016 | Spence et al. | |
| 2016/0256276 A1 | 9/2016 | Yaron | |
| 2016/0346080 A1 | 12/2016 | Righini et al. | |
| 2017/0007399 A1 | 1/2017 | Keranen | |
| 2017/0007402 A1 | 1/2017 | Zerkowski et al. | |
| 2017/0217385 A1 | 8/2017 | Rinkleff et al. | |
| 2017/0266005 A1 | 9/2017 | McGuckin, Jr. | |
| 2017/0273788 A1 | 9/2017 | O'Carroll et al. | |
| 2017/0273789 A1 | 9/2017 | Yaron et al. | |
| 2017/0281337 A1 | 10/2017 | Campbell | |
| 2018/0000580 A1 | 1/2018 | Wallace et al. | |
| 2018/0085217 A1 | 3/2018 | Lashinski et al. | |
| 2018/0206074 A1 | 7/2018 | Tanasa et al. | |
| 2018/0289481 A1 | 10/2018 | Dolan | |
| 2018/0303606 A1 | 10/2018 | Rothstein et al. | |

(56) References Cited

U.S. PATENT DOCUMENTS

2018/0318073 A1 11/2018 Tseng et al.
2018/0318080 A1 11/2018 Quill et al.

FOREIGN PATENT DOCUMENTS

| | | |
|---|---|---|
| EP | 0592410 B1 | 10/1995 |
| EP | 0850607 A1 | 7/1998 |
| EP | 1432369 A1 | 6/2004 |
| EP | 1521550 A2 | 4/2005 |
| EP | 1296618 B1 | 1/2008 |
| EP | 1827314 B1 | 12/2010 |
| EP | 2620125 A1 | 7/2013 |
| EP | 2726018 A2 | 5/2014 |
| EP | 2806829 A2 | 12/2014 |
| WO | 9117720 A1 | 11/1991 |
| WO | 0149213 A2 | 7/2001 |
| WO | 0154625 A1 | 8/2001 |
| WO | 0247575 A2 | 6/2002 |
| WO | 03028558 A2 | 4/2003 |
| WO | 2005084595 A1 | 9/2005 |
| WO | 2006011127 A2 | 2/2006 |
| WO | 2005102015 A3 | 4/2007 |
| WO | 2007067942 A1 | 6/2007 |
| WO | 2009155561 A2 | 12/2009 |
| WO | 2010121076 A2 | 10/2010 |
| WO | 2012063228 A1 | 5/2012 |
| WO | 2013110722 A2 | 8/2013 |
| WO | 2013114214 A2 | 8/2013 |
| WO | 2015023579 A1 | 2/2015 |
| WO | 2015023862 A2 | 2/2015 |
| WO | 2015127264 A1 | 8/2015 |
| WO | 2015198125 A1 | 12/2015 |
| WO | 2016038017 A1 | 3/2016 |
| WO | 2016040881 A1 | 3/2016 |
| WO | 2016130820 A1 | 8/2016 |
| WO | 2017103833 A1 | 6/2017 |

CARDIAC VALVE REPAIR SYSTEM AND METHODS OF USE

RELATED APPLICATIONS

This application is a continuation of U.S. application Ser. No. 16/146,073, filed Sep. 28, 2018, entitled "Cardiac Valve Repair System and Methods of Use," which names Jacques Seguin as an inventor, and which is a division of U.S. application Ser. No. 15/494,107, filed Apr. 21, 2017, entitled "Cardiac Valve Repair System and Methods of Use," which names Jacques Seguin as an inventor, and which is a continuation of U.S. application Ser. No. 14/188,442, filed Feb. 24, 2014, now U.S. Pat. No. 9,629,716, entitled "Cardiac Valve Repair System and Methods of Use," which names Jacques Seguin as an inventor, and which is a division of U.S. application Ser. No. 12/839,363, filed on Jul. 19, 2010, now U.S. Pat. No. 8,657,872, entitled "Cardiac Valve Repair System and Methods of Use," which names Jacques Seguin as inventor, each of which is incorporated by reference herein in their entirety.

FIELD OF THE INVENTION

This application generally relates to apparatus and methods for performing transcatheter or minimally invasive repair or replacement of a cardiac valve, such as the mitral valve, by anchoring an expandable replacement valve body to the leaflets of an incompetent cardiac valve.

BACKGROUND OF THE INVENTION

In recent years a wide array of replacement cardiac valves have been proposed for treating cardiac valve diseases, such as valve regurgitation or stenosis. The human heart contains four valves that separate the atria from the lungs and ventricles: The tricuspid valve disposed between the right atrium and right ventricle, the pulmonary valve disposed between the right ventricle and the pulmonary artery, the bicuspid (or mitral) valve disposed between the left atrium and the left ventricle, and the aortic valve disposed between the left ventricle and the aorta. Each of these valves has a slightly different anatomy than the others, requiring differently-designed replacement valve solutions.

For example, whereas U.S. patent application Ser. No. US 2006/0265056 to Nguyen et al. describes a catheter-delivered aortic valve having a self-expanding stent that causes the valve to become anchored to the valve annulus, such a solution may not be feasible for repair of a mitral valve due to the possibility that the self-expanding stent may occlude the left ventricle outflow tract for the adjacent aortic valve. Accordingly, it would be desirable to provide a transcatheter or minimally-invasive cardiac valve repair system that can employ a replacement valve disposed in an expandable stent body, but that avoids potential disadvantages of the prior art.

In view of the drawbacks attendant upon using expandable stents for some cardiac valve repair procedures, the state-of-the-art for previously-known cardiac repair procedures has been surgical repair or replacement of defective valves. For example, mitral valve repair currently is handled as an open surgical procedure, in which the defective valve leaflets are cut away and a new valve body, employing either natural tissue or synthetic fabric, is sewn to the valve annulus. U.S. Pat. No. 4,490,859 to Black et al. describes such a replacement valve, which comprises a polymer frame mounted on a sewing ring, wherein the frame is covered by an animal tissue or synthetic fabric frame.

Other previously-known attempts to repair mitral valves using a minimally invasive or catheter-based approach have sought to reduce the time, skill and effort required to attach the replacement valve to the existing valve annulus using barbs or spring-like clips as described, for example, in U.S. Pat. No. 7,101,395 to Tremulis et al. U.S. Pat. No. 6,419,696 to Ortiz et al. describes a mitral valve repair system comprising a double helix structure that may delivered via catheter or a minimally-invasive route so that upper and lower rings of the double helix sandwich the valve leaflets and increase the rigidity of the leaflets, thus reducing regurgitation. That patent further describes that its double helix structure may be used to anchor a valve body having a fixed outer circumference that is delivered via a surgical or minimally-invasive route. Neither of the valve repair systems described in the foregoing patents permits installation of a replacement cardiac valve body using a purely transcatheter delivery route.

In view of the above-noted drawbacks of previously-known systems, it would be desirable to provide methods and apparatus for delivering a replacement cardiac valve via a transcatheter approach, either transvascularly or via a minimally-invasive approach.

It also would be desirable to provide a replacement cardiac valve, and methods of using same, that may be deployed with reduced risk of obstructing an outflow tract of an adjacent cardiac valve.

It further would be desirable to provide a replacement cardiac valve, and methods of using same, wherein the anchor used to fasten an expandable cardiac valve body limits expansion of the cardiac valve body to a predetermined size and shape.

It still further would be desirable to provide a replacement cardiac valve, and methods of using same, wherein the replacement cardiac valve is configured to firmly anchor the valve body to the pre-existing cardiac valve leaflets, while reducing the risk of perivalvular leakage.

It also would be desirable to provide a replacement cardiac valve, and methods of using same in which, in some embodiments, an anchor of the replacement cardiac valve reshapes the pre-existing valve annulus to accommodate alternative replacement valve body configurations.

SUMMARY OF THE INVENTION

The present invention provides a replacement cardiac valve, and methods of using same, that overcomes the drawbacks of previously-known systems. Exemplary embodiments of the present invention include an anchor comprising a double helix configured to engage the cardiac valve leaflets of a diseased or defective cardiac valve, and replacement valve body disposed in an expandable stent that is disposed within the anchor, such that the anchor limits expansion of the expandable stent portion of the replacement cardiac valve. The expandable stent of the replacement valve body may be self-expanding or mechanically expanded, e.g., using a balloon catheter or catheter-based mandrel.

In some embodiments the replacement valve body may comprise a metal alloy or polymer frame covered by animal tissue or synthetic fabric that mimics the valve configuration of the valve being replaced. Alternatively, the valve body may comprise any suitable valve structure suitable for transcatheter delivery.

In accordance with one aspect of the invention, the anchor and replacement valve body may be implanted using a transvascular approach. Implantation of a mitral valve embodiment of the present invention, for example, may be accomplished by passing a catheter through the femoral vein into the right atrium, followed by a transeptal puncture to gain access to the mitral valve from above. Alternatively, a minimally-invasive approach may be used wherein a catheter is inserted through a keyhole opening in the chest and catheter is inserted transapically from below the mitral valve. In either case, the anchor component of the present invention may then be deployed first, after which the replacement valve body may be deployed within anchor. As a further alternative, the replacement valve body may be pre-attached to the anchor such that the device may be implanted in a single step.

In accordance with another aspect of the present invention, the expandable stent of the replacement valve body may include a feature, e.g., a reduced diameter section, that is configured to engage the anchor component to reduce the potential for movement of the replacement valve body relative to the anchor. In still other embodiments, expansion of the expandable stent against the anchor may secure the anchor into engagement with the cardiac valve leaflets. In yet further embodiments, the double helix of the anchor may expand during deployment from a delivery configuration that facilitates insertion of a lower ring of the double helix into engagement with the ventricular surfaces of the leaflets and a deployed configuration wherein the double helix assumes an ovoid configuration that approximates the natural shape of the cardiac valve annulus. Alternatively, the double helix of the anchor transitions from a small diameter ring to a larger diameter ring, such that the anchor remodels the shape of cardiac valve annulus, e.g., from a substantially ovoid shape to a substantially circular shape.

Methods of using the replacement cardiac valve system of the present invention also are provided.

BRIEF DESCRIPTION OF THE DRAWINGS

FIGS. 1A and 1B show an exemplary embodiment of a replacement cardiac valve system constructed in accordance with the principles of the present invention, wherein FIG. 1A shows a sectional view in the deployed state and FIG. 1B shows a side view in the delivery state.

DETAILED DESCRIPTION OF THE INVENTION

Figure 1A:
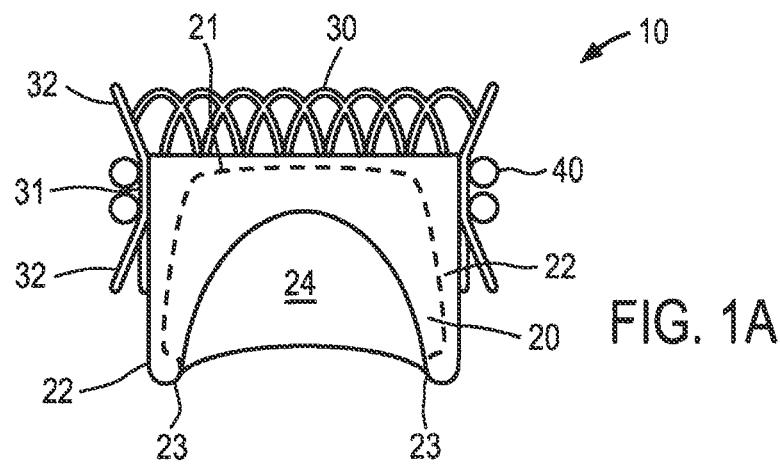
Figure 1B:
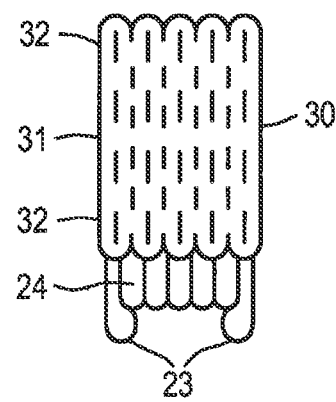

Referring to FIGS. 1A and 1B, an illustrative embodiment of a cardiac repair system constructed in accordance with the principles of the present invention is described. Illustratively, the cardiac valve is designed for replacement of a defective mitral valve, although it could be readily adapted for other cardiac valves. Replacement cardiac valve 10 includes animal tissue or synthetic valve body 20 mounted in expandable stent 30. Anchor 40 comprising a double helix of a metal alloy is shown engaged on the exterior of stent 30. Replacement cardiac valve 10 has an expanded, deployed state, shown in FIG. 1A, and a contracted delivery state, shown in FIG. 1B, such that the device may be disposed within a delivery catheter for transvascular or minimally-invasive surgical delivery. In FIG. 1B, anchor 40, which is separately delivered for this embodiment, is omitted.

For purposes of illustration only, expandable stent 30 comprises a self-expanding stent constructed using woven metal alloy wires or any of a number of cell patterns cut into a metal alloy tube, using any of a number of previously-known stent making techniques. Stent 30 may include waist portion 31 disposed between upper and lower flared cods 32, which are configured to engage anchor 40, described below, to reduce or prevent stent 30 from moving relative to anchor 40 once deployed. Stent 30 may comprise a superelastic material, such as a nickel-titanium alloy, that is treated to expand from the contracted delivery state to the expanded deployed state by isothermal or thermal conversion of a martensitic state to an austenitic state of the alloy. Alternatively, expandable stent 30 may comprise non-superelastic metal alloy, such as stainless steel or cobalt-chrome alloy, that may be compressed onto a balloon catheter and then plastically expanded during deployment. Expandable stent 30 may comprise any expandable cell pattern known in the stent art suitable for providing the range of increases in stent diameter and sufficient rigidity to prevent the stent from moving once deployed.

Valve body 20 illustratively is constructed as described in U.S. Pat. No. 4,490,859 to Black et al., which is incorporated herein by reference, and comprises treated animal tissue, such as porcine, bovine or equine pericardial tissue, or any of a number of synthetic fabrics, such as a polyethylene terephthalate fabric, e.g., DACRON® (a registered trademark of Invista North America S.A.R.L. Corporation), mounted on a collapsible metal alloy or polymer frame. The collapsible frame 21 (shown in dotted line) preferably includes a pair of upstanding posts 22 disposed on opposite sides of the frame to form commissural points 23 for the tissue or synthetic fabric leaflets 24. As described in the foregoing patent, the tissue or fabric components of the valve body are cut from flat pieces of material, and then sewn or bonded together, and to the pair of upstanding posts and expandable stent, to form a semilunar valve that mimics the functionality of an intact non-diseased mitral valve. Alternatively, valve body 20 may be of any construction suitable to be collapsed to a reduced diameter so as to permit the expandable stent and attached valve body to be delivered via catheter in a contracted delivery state.

In accordance with one aspect of the present invention, anchor 40 comprises a helix structure having at least two turns and configured such that one turn of the helix is configured to engage the atrial surface of the cardiac valve leaflets while the other contacts the ventricular surface of the leaflets. Preferably, the anchor comprises a superelastic material that is trained to transform from a substantially straight wire, when disposed within a delivery catheter, to a double helix structure when extruded from the delivery catheter and/or heated. An example of thermally-induced transformation is described in U.S. Pat. No. 4,512,338 to Balko et al., while a similar isothermal transition from stress-induced martensite to austenite is described in U.S. Pat. No. 6,306,141 to Jervis. As described below, the helical anchor performs three functions in the context of the present invention. First, the anchor serves to secure the replacement valve to the mitral valve leaflets without contacting the entire circumference, and potentially, without contacting any portion of the existing valve annulus—thereby reducing the risk that the replacement cardiac valve will obstruct the outflow tract of an adjacent cardiac valve. Second, the anchor, when fully deployed, limits expansion of the expandable stent, and thus ensures that the replacement valve body cannot overexpand during deployment. In this manner, the predetermined diameter of the anchor ensures, e.g., that no gaps can form between the leaflets of the replacement valve body caused by overexpansion of the expandable stent. Third, the anchor serves to retain the edges of the cardiac valve beyond the periphery of the anchor in approximation, thus reducing the risk of perivalvular leaks arising around the replacement cardiac valve.

Figure 2:
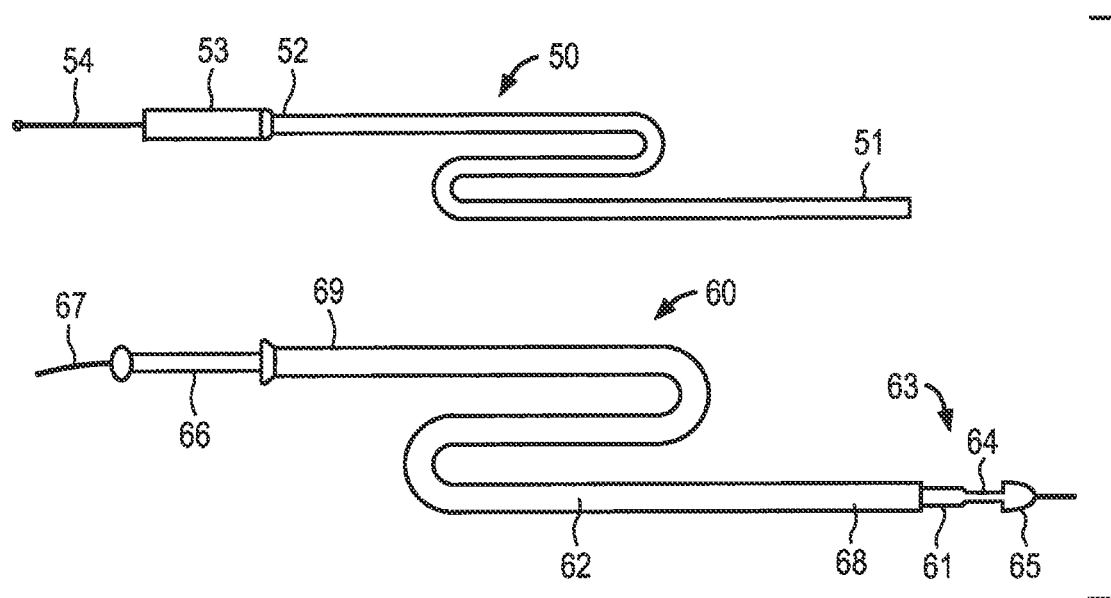
FIG. 2 depicts illustrative embodiments of catheters for transvascular delivery of the anchor and valve body components of the present invention.

Referring now to FIG. 2, an exemplary embodiment of a two-piece delivery system for the replacement cardiac valve of the present invention is described. Anchor delivery catheter 50 comprises a suitable length of tubing having distal end 51, proximal end 52, an internal lumen extending therebetween, handle portion 53, and push rod 54 disposed in the internal lumen. As described below in detail with respect to the method of implanting the replacement cardiac valve of the present invention, helical anchor 40 may be straightened and inserted into the lumen of catheter 50 so that its proximal end abut against a distal end of push rod 54. The proximal end of the straightened anchor 40 may be engaged with the distal end of push rod 54, e.g., by gripping jaws such as depicted in FIG. 6B of U.S. Pat. No. 6,419,696 to Ortiz et al., or may include male and female threaded ends that interengage.

In the context of a mitral valve repair system, distal end 51 of catheter 50 may be configured, for example, to be routed transvascularly through an opening in the patient's femoral vein, through the right atrium and an atrial transeptal puncture into the left atrium. Once so positioned, pushrod 54 may be advanced to extrude the anchor from within the lumen of catheter 50 to engage the cardiac valve leaflets, as explained below. Alternatively, distal end 51 of catheter may be brought into engagement with mitral valve via a minimally-invasive surgical approach, in which the catheter is advanced towards the ventricular side of the mitral valve through a transapical opening in the left ventricle.

Still referring to FIG. 2, valve delivery catheter 60 illustratively comprises inner shaft 61 slidably disposed in sheath 62. Inner shaft 61 includes distal end 63 having recessed portion 64, bullet-nosed atraumatic end 65, proximal end 66, and an optional guide wire lumen extending throughout the length of inner shaft 61 to accept guide wire 67. Sheath 62 includes distal end 68 and proximal end 69, and is disposed on inner shaft 61 so that distal end 68 of sheath 62 may be selectively retracted to uncover recess 64 on inner shaft 61. Catheters 50 and 60 preferably comprises materials conventionally used in catheter designs, and have lengths and profiles suitable for the selected access path, i.e., either transvascular or transapical. Recess 64 is sized to permit expandable stent 30 and valve body 20 to be compressed within, and retained within, the recessed portion for delivery when covered by sheath 62. Alternatively, for plastically deformable embodiments of expandable stent 30, recess 64 on inner shaft 61 may be replaced by an expandable balloon configured, as is conventional in the art of balloon-expandable stents, to be inflated to deploy the expandable stent and valve body within the helical anchor.

Figure 3:
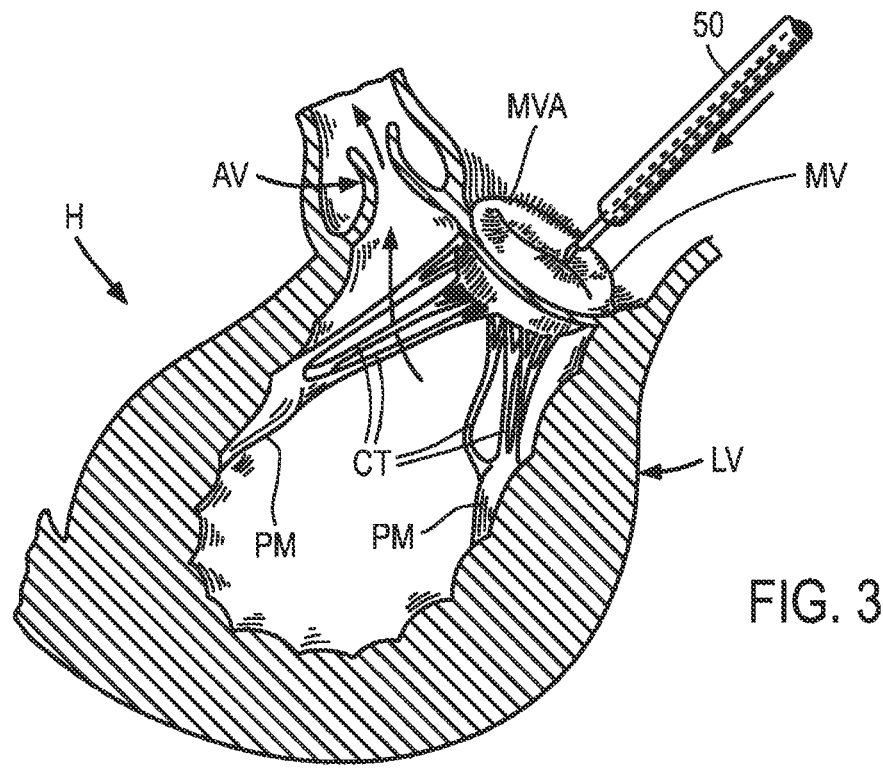
FIG. 3 is a sectional view of the left ventricular portion of a human heart showing a mitral valve being repaired using the replacement cardiac valve system of the present invention, wherein the delivery catheter for the anchor has been disposed proximate the atrial surface of the mitral valve.

Referring to FIG. 3, a method of deploying the cardiac replacement valve of present invention is now described in the context of repairing a defective mitral valve. In FIG. 3, the left ventricular quadrant of a human heart H is shown having mitral valve MV located within mitral valve annulus MVA. The leaflets of the mitral valve are tethered to the endocardium of the left ventricle LV via the chordae tendineae CT and papillary muscles PM. The outflow tract of the aortic valve AV is disposed immediately adjacent to mitral valve. As discussed above, this anatomical feature of the mitral valve makes anchoring an expandable stent directly to the mitral valve annulus problematic, since it creates a risk that expandable stent will obstruct the outflow tract for the aortic valve. Alternatively, having an expandable stent expanded into direct engagement with the mitral valve annulus may disrupt or remodel the aortic valve annulus, causing mismatch of the leaflets of that valve and possibly aortic valve regurgitation.

In FIG. 3, anchor delivery catheter 50 is shown approaching the mitral valve with a portion of helical anchor 40 extending from the distal end of the catheter. In accordance with one aspect of the present invention, helical anchor 40 is inserted through the opening between the mitral valve leaflets so that, when the helical anchor expands, the portion of the anchor passing between the leaflets preferably settles into one of two opposite commissural regions between the leaflets.

Figure 4A:
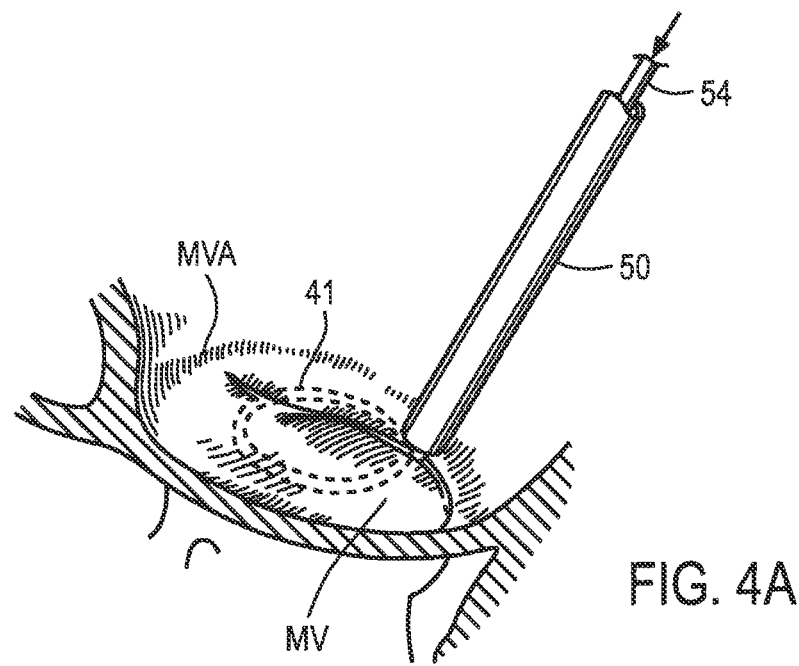
FIGS. 4A, 4B and 4C are illustrative views showing deployment of the anchor component of the present invention in contact with the ventricular surface of a mitral valve undergoing repair.
Figure 4B:
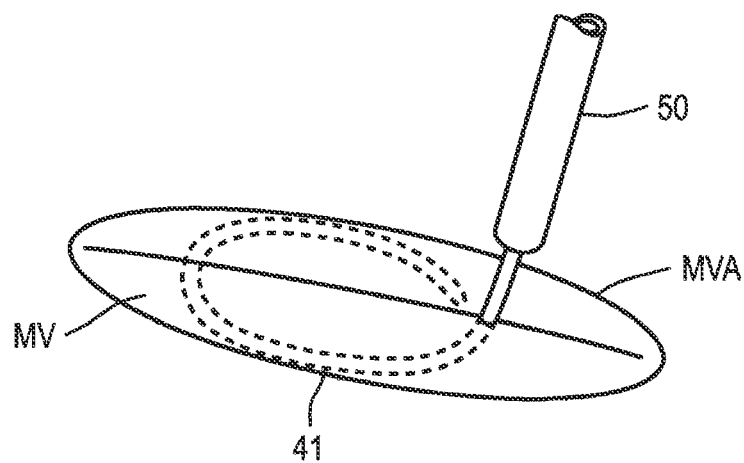
Figure 4C:
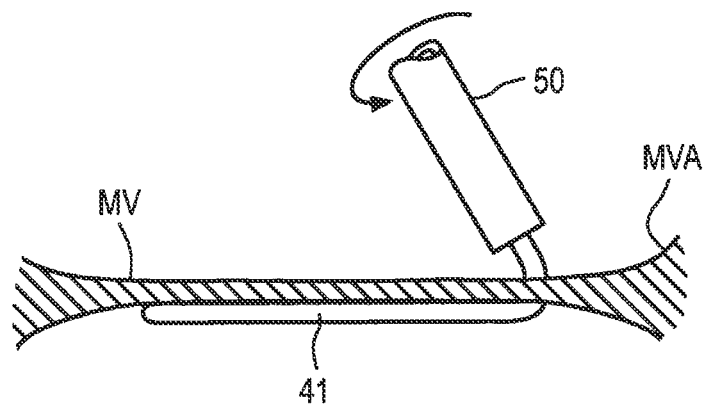
Figure 5B:
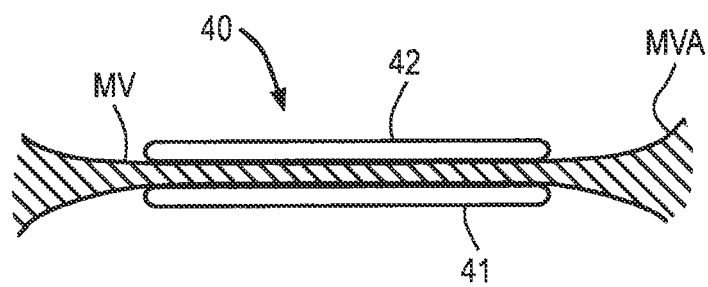
FIGS. 5A and 5B are, respectively, a perspective view and side sectional view showing the anchor component of the present invention fully deployed on the leaflets of a mitral valve.
Figure 5A:
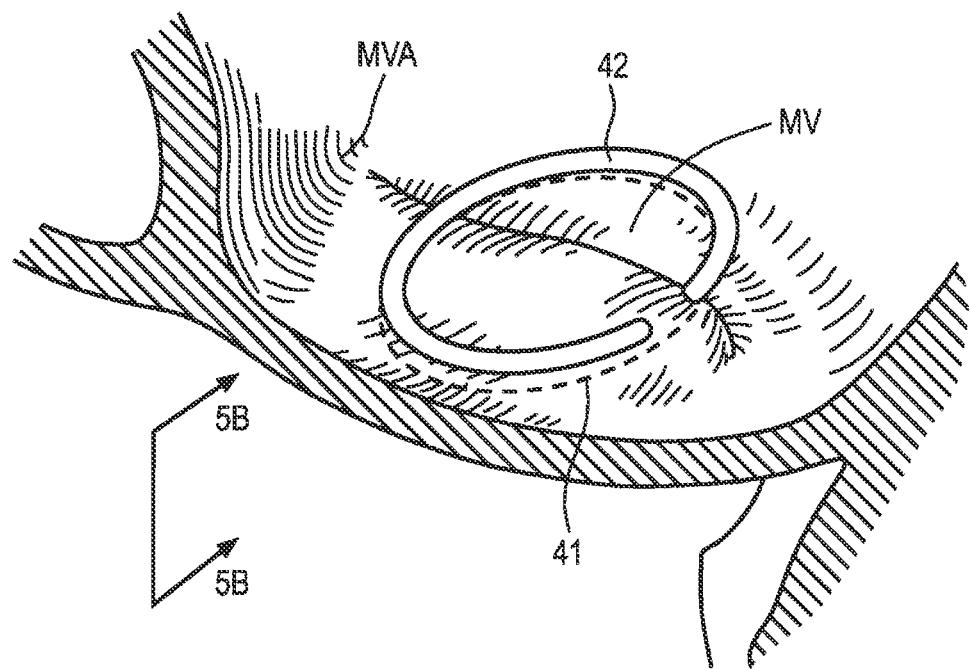

Referring now to FIGS. 4A through 4C, as shown in FIG. 4A, anchor 40 continues to be extruded from anchor delivery catheter 50 in contact with the ventricular side of mitral valve MV, the anchor forms a substantially circular helical turn 41. Helical turn 41 expands until it contacts the anterior and posterior edges of the mitral valve annulus, as depicted in FIG. 4B. As shown in FIGS. 5A and 5B, once lower helical turn 41 is delivered, catheter 50 may be rotated, e.g., by rotating the handle 53 of anchor delivery catheter 50 while observing deployment of helical anchor 40 under fluoroscopic guidance, so that upper helical turn 42 is disposed on the atrial surface of the leaflets in registration with lower helical turn 41. Catheter 50 then is withdrawn, leaving the helical anchor disposed with lower helical turn 41 and upper helical turn 42 sandwiching the leaflets of the mitral valve therebetween.

Figure 6A:
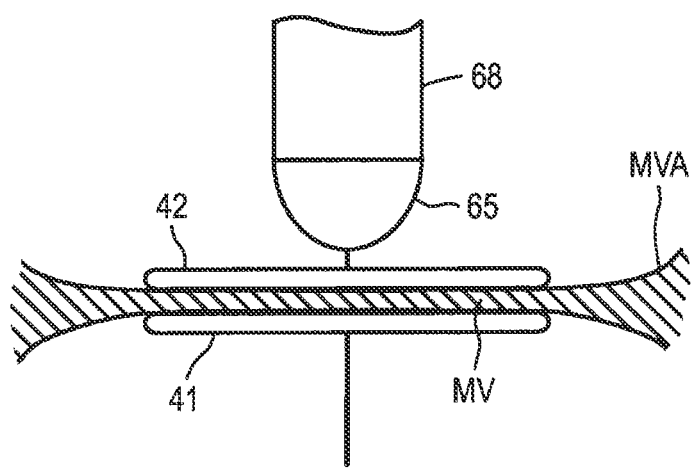
FIGS. 6A and 6B depicts the distal end of the replacement valve body delivery catheter shown in FIG. 2 approaching, and penetrating, respectively, the mitral valve of FIG. 5 on which the anchor has been deployed.
Figure 6B:
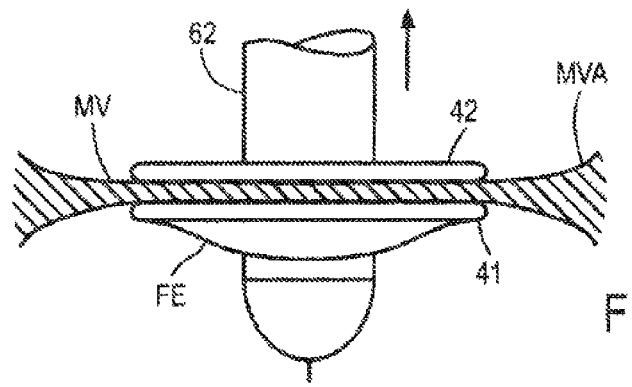

Next, wire guide 67 is routed through the mitral valve leaflets and, as depicted in FIG. 6A, valve delivery catheter 60 is advanced along the guide wire until bullet-nosed end cap 65 passes through the leaflets. As distal end 63 of catheter 60 passes through the leaflets, free ends FE of the leaflets deflect downward as depicted in FIG. 6B. As will be understood, only the nearer leaflet along view line 5B-5B is visible in FIG. 6B; the free ends FE of both leaflets would be visible along a view line at a 90-degree angle from view line 5B-5B along the circumference of the mitral valve annulus. Free ends FE of the leaflets will be trapped between the expandable stent and the inner circumference of lower helical turn 41 when the expandable stent and valve body are deployed within the helical anchor. Alternatively, the portions of the mitral valve leaflets that extend within the circumference of the helical anchor may be removed using conventional transcatheter cutting means, e.g., using atherectomy catheter as described in U.S. Pat. No. 6,235,042 to Katzman. Distal end 63 of catheter 60 then is advanced, e.g., by monitoring radiopaque markers (not shown) on inner shaft 61 or sheath 62 under fluoroscopic guidance to confirm that waist 31 of expandable stent 30 is aligned with anchor 40.

Figure 7:
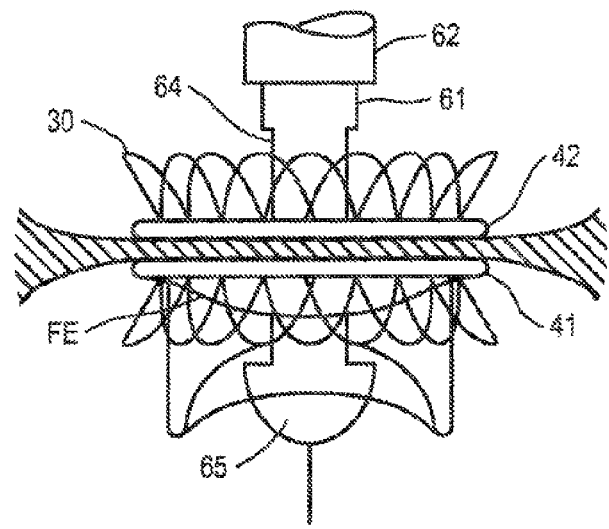
FIG. 7 is a side view showing deployment of the replacement valve body from the delivery catheter.

As depicted in FIG. 7, after proper positioning of expandable stent 30 has been confirmed, inner shaft 61 of catheter 60 is held stationary while sheath 62 is retracted proximally to uncover replacement cardiac valve 10. As sheath 62 is retracted, expandable stent 30 self-expands until it contacts the inner circumference, of helical anchor 40. In particular, waist 31 of expandable stent 30 contacts the inner circumference of helical turn 42 of anchor 40, while the lower portion of waist 31 expands until it traps the free ends of the mitral valve leaflets against the inner circumference of lower helical turn 41 of anchor 40. As described, for example, in U.S. Patent Publication No. US 2006/0265056, valve body 20 is coupled to expandable stent 30 so that it deploys as stent 30 expands. Thus, self-expansion of expandable stem 30 also causes valve body 20 to open to its fully deployed and functional position. Distal end 63 of catheter 60 and guide wire 67 are then withdrawn, completing implantation of the replacement cardiac valve.

In an alternative embodiment, waist 31 of the expandable stent may be substantially omitted, such that expandable stent comprises upper and lower flared ends that meet at the mid-height of the stent, for example, as depicted in U.S. Pat. No. 6,120,534 to Ruiz. In this case, when the stent expands, it will generate forces on lower helical turn 41 and upper helical turn 42 of anchor 40 that urge the turns towards one another, thereby enhancing the grip of the helical anchor on the mitral valve leaflets.

In a yet further alternative embodiment, expandable stent 30 may comprise a plastically deformable stent that is expanded to its expanded, deployed state using a balloon catheter or expanding mandrel. Preferably, the balloon should be configured, e.g., using multiple spaced-apart lobes so as to not crush valve body 20 during deployment of the stent. In this case, the expandable stent may have a uniform diameter in the contracted delivery position. During deployment of the expandable stent, the stent will expand to the limits permitted by the inner circumference of the helical anchor, while the unrestrained upper and lower portions of the stent beyond the helical anchor will tend to expand slightly more, thus locking the stent into engagement with the helical anchor, and urging the upper and lower helical turns of the anchor into secure engagement with the mitral valve leaflets.

In accordance with the principles of the present invention, helical anchor 40 serves several functions: (1) it secures the replacement valve to the mitral valve leaflets without contacting the entire circumference; (2) it limits expansion of the expandable stent, and ensures that the replacement valve body cannot over-expand during deployment; and (3) it retains the free edges of the cardiac valve beyond the periphery of the anchor in approximation, thus reducing the risk of perivalvular leaks. As will be observed from the anatomy of the mitral valve depicted in FIG. 3, for example, it may not be possible to expand a self-expanding or balloon-expandable stent into direct contact with the mitral valve annulus since the lower end of the stent body may partially obstruct the outflow tract of the adjacent aortic valve. Instead, by placing the helical anchor of the present invention so that it is supported by the mitral valve leaflets, the present invention ensures that the lower end of the expandable stent and valve body do not interfere with the outflow tract of the left ventricle. In addition, because the helical anchor of the present invention preferably contacts at most only the anterior and posterior portions of the mitral valve annulus, there is reduced risk that the expandable stent of the replacement cardiac valve of the present invention will undesirably remodel the adjacent aortic valve, and thus little risk that repairing the mitral valve will lead to a defect in the adjacent aortic valve. Moreover, because the helical anchor limits expansion of the expandable stent to the predetermined inner diameter of the anchor, it ensures that valve body 20 reproducibly deploys to a predetermined diameter regardless of the patient's particular, and thus no gaps should form between the leaflets of the replacement valve body caused by overexpansion of the expandable stent. Finally, because the upper and lower helical turns of helical anchor 40 securely engage the free ends of the mitral valve leaflets, the inventive system is expected not to suffer from perivalvular leaks.

Figure 8:
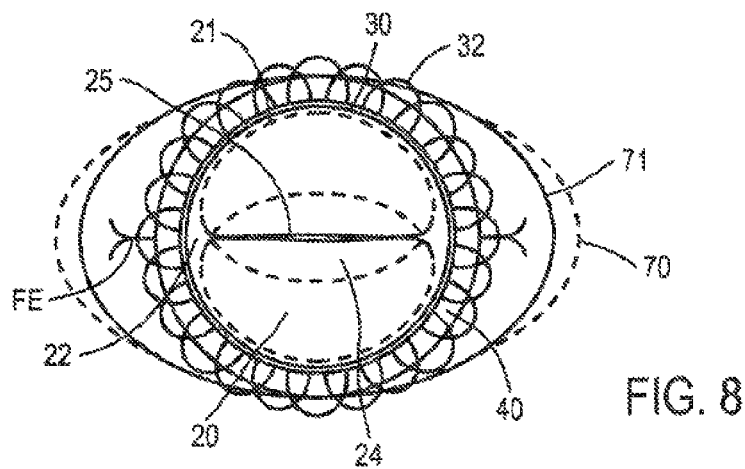
FIG. 8 is a view from the atrial side of the mitral valve that undergone repair using the cardiac valve replacement system of the present invention.

With respect to FIG. 8, replacement cardiac valve system 10 is described, as viewed from within the left atrium, after deployment in the mitral valve annulus. Upper helical turn 41 of anchor 40 is visible surrounding expandable stent 30, with the cells of the upper flared portion 32 overhanging anchor 40. Valve body 20 is visible within expandable stent 30, including collapsible frame 21, posts 22 and synthetic fabric leaflets 24, the free ends of which coapt to create valve opening 25. Also shown in FIG. 8 are free ends FE of the pre-existing valve leaflets, which are secured against one another by anchor 40, and in some embodiments a compressive force applied by expandable stent 30 as discussed above. As can be further seen in FIG. 8, each of the free outer edges of the commissural regions between the pre-existing valve leaflets can extend radially beyond the periphery of the anchor 40.

In accordance with one aspect of the present invention, anchor 40 contacts the anterior and posterior edges of the mitral valve annulus, and may remodel the valve annulus to a limited extent to provide the desired cross-sectional area for flow passing through valve body 20, for example, by increasing the length of the minor axis of the valve white decreasing the length of the major axis of the valve (shown by change from the dotted line 70 to the solid line 71). Advantageously, this remodeling effect, if present, is not expected to interfere with the annulus shape of, or approximation of the leaflets of, the adjacent aortic valve.

As will be appreciated by one of ordinary skill, valve body 20 may comprise flow control mechanisms, such as leaflets, balls, flap valves, duck-billed valves, etc., such as art known in the art, without departing from the spirit of the present invention, so long as such valve configurations can be contracted to a reduced delivery state for transcatheter minimally invasive implantation within anchor 40. In addition, anchor 40 may comprise, for example, a suitably trained shape memory alloy, that expands to non-circular expanded, deployed shape, such as an ovoid or D-shaped configuration. In this latter case, valve body 20 should be configured so that, when expandable stent 30 is fully deployed within anchor 40, the valve body expands to a predetermined shape with the required level of coaptation.

Although the embodiments described above contemplate separately delivering anchor 40 from the assembled replacement valve body 20 and expandable stent using the separate catheters discussed above in FIG. 2, all components could be delivered using a single catheter having multiple lumens from which the anchor and remainder of the replacement cardiac valve are delivered. Alternatively, anchor 40 may be attached to the expandable stent and valve body, such that the anchor is first deployed and rotated into position on the valve leaflets, and then the expandable stent and valve body are deployed.

Figure 9A:
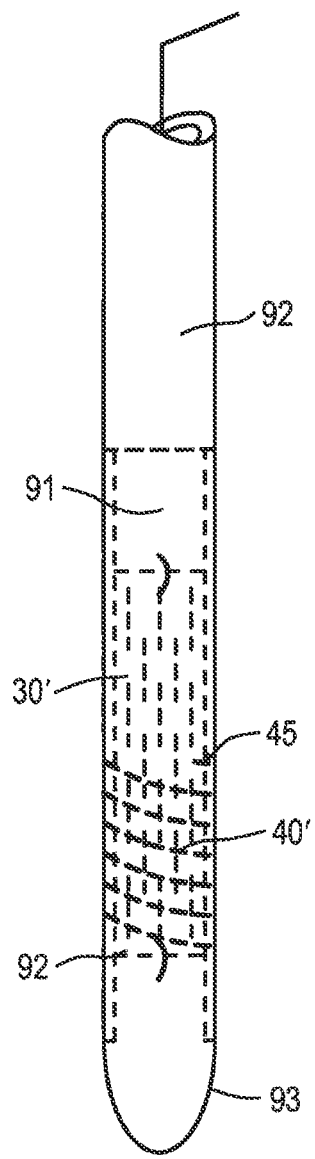
FIGS. 9A and 9B are schematic illustrations of an alternative embodiment of the cardiac replacement valve system of the present invention in which the anchor is pre-attached to expandable stent and replacement valve body.
Figure 9B:
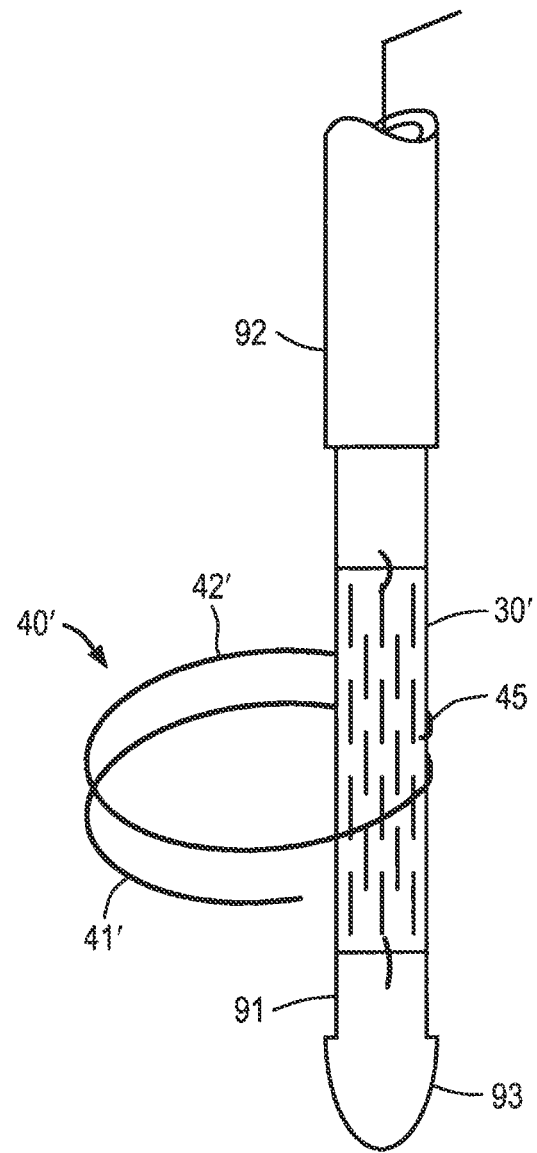

Referring now to FIGS. 9A and 9B, replacement cardiac valve 80 of the present invention is described, in which like components of the embodiment of FIG. 1 and denoted by like-primed numbers. In FIG. 9A., replacement cardiac valve 80 is schematically shown disposed on delivery catheter 90, such that expandable stent 30' including the replacement valve body (not visible in FIG. 9A) is contracted within recess 91 of inner shaft 92, Sheath 93 is slidably disposed on inner shaft 92 so that it can be retracted proximally to expose replacement cardiac valve 80.

In FIG. 9A, anchor 40' is wrapped in multiple helical turns around the body of expandable stent 30', and is fastened to expandable stent 30' at fixed end 45. Sheath 92 retains anchor 40' wound down on the exterior of expandable stent until bullet-nose 93 of delivery catheter is inserted through the leaflets of the cardiac valve to be repaired, in a manner similar to that depicted in FIG. 6B above. In addition, one or more lock wires 94 extend from the proximal end to the distal end of catheter 90 to secure expandable stent 30 to inner shaft 91 in a manner similar to that disclosed, for example, in U.S. Pat. No. 5,443,500 to Sigwart. As will be understood by one of ordinary skill, lock wires 94 may be retracted proximally to deploy a self-expanding embodiment of expandable stent 30' as described for the preceding embodiments. Alternatively, if expandable stent 30' is balloon expandable, lock wires 94 may be omitted.

Once replacement cardiac valve 80 is disposed across the valve to be repaired, as may be determined, e.g., using fluoroscopy, sheath 92 is retracted proximally as shown in FIG. 9B to allow anchor 40' to unwind to its deployed shape having at least two helical turns, 41' and 42'. Catheter 90 then may be rotated to pass the free end of helical turn 41' between the leaflets until anchor 40' fully engages the atrial and ventricular surfaces of the leaflets to sandwich the leaflets between helical turns 41' and 42' in the manner depicted in FIG. 5B. Lock wires 94 then are retracted proximally to disengage expandable stent 30', causing the expandable stent and valve body disposed therein to self-expand into engagement with anchor 40'. Alternatively, if expandable stent 30' is mechanically expanded, the balloon or mandrel may be actuated to expand stent 30' and the replacement valve body into engagement with helical anchor 40' in a manner similar to that shown in FIGS. 7 and 8.

While various illustrative embodiments of the invention are described above, it will be apparent to one skilled in the art that various changes and modifications may be made therein without departing from the invention. The appended claims are intended to cover all such changes and modifications that fall within the true spirit and scope of the invention.

The invention claimed is:

1. A replacement valve for a cardiac valve, comprising:
a helical anchor configured to be extruded through a delivery catheter, the helical anchor comprising an upper turn configured to be deployed on an atrial side of the cardiac valve and a lower turn configured to engage a ventricular side of one or more leaflets of the cardiac valve;
an expandable stent configured to transition from a contracted delivery state to an expanded deployed state wherein expansion of the expandable stent from the contracted delivery state to the expanded deployed state is configured to trap the one or more leaflets of the cardiac valve between the expandable stent and the lower turn of the helical anchor;
a valve body disposed within the expandable stent;
wherein the helical anchor limits expansion of the expandable stent;
wherein the helical anchor is configured to transition between an elongated delivery state enabling transcatheter delivery and an expanded, helical deployed state; and
wherein the lower turn of the helical anchor, in the expanded, helical deployed state, is configured to have a diameter smaller than a major axis of the cardiac valve, such that native commissural regions of the cardiac valve extend radially beyond the lower turn.

2. A replacement valve for a cardiac valve, comprising:
a helical anchor configured to be extruded through a delivery catheter, the helical anchor comprising an upper turn configured to be deployed on an atrial side of the cardiac valve and a lower turn configured to engage a ventricular side of one or more leaflets of the cardiac valve;
an expandable stent configured to transition from a contracted delivery state to an expanded deployed state wherein expansion of the expandable stent from the contracted delivery state to the expanded deployed state is configure to trap the one or more leaflets of the cardiac valve between the expandable stent and the lower turn of the helical anchor;
a valve body disposed within the expandable stent;
wherein the helical anchor limits expansion of the expandable stent; and
wherein the expandable stent in the expanded deployed state is configured to have a diameter smaller than a major axis of the cardiac valve, such that native commissural regions of the cardiac valve extend radially beyond the expandable stent in the expanded deployed state.

3. A replacement valve for a cardiac valve, comprising:
a helical anchor configured to be extruded through a delivery catheter, the helical anchor comprising an upper turn configured to be deployed on an atrial side of the cardiac valve and a lower turn configured to engage a ventricular side of one or more leaflets of the cardiac valve;
an expandable stent configured to transition from a contracted delivery state to an expanded deployed state wherein expansion of the expandable stent from the contracted delivery state to the expanded deployed state is configure to trap the one or more leaflets of the cardiac valve between the expandable stent and the lower turn of the helical anchor;
a valve body disposed within the expandable stent;
wherein the helical anchor limits expansion of the expandable stent; and
wherein the expandable stent, when implanted, is configure to not contact an entire circumference of a valve annulus of the cardiac valve.

4. A method of repairing a cardiac valve of a heart, comprising:
inserting a first turn of a helical anchor through an opening defined by valve leaflets of the cardiac valve, such that the first turn is deployed in a ventricle of the heart, wherein the first turn engages a ventricular side of the cardiac valve;

deploying a second turn of the helical anchor in an atrium of the heart;

deploying an expandable stent within the helical anchor such that, upon expansion, one or more leaflets of the cardiac valve are trapped between the expandable stent and the first turn of the helical anchor;

wherein a replacement valve body is disposed within the expandable stent;

wherein the helical anchor limits expansion of the expandable stent; and wherein the expandable stent is self-expanding.

5. A method of repairing a cardiac valve of a heart, comprising:

inserting a first turn of a helical anchor through an opening defined by valve leaflets of the cardiac valve, such that the first turn is deployed in a ventricle of the heart, wherein the first turn engages a ventricular side of the cardiac valve;

deploying a second turn of the helical anchor in an atrium of the heart;

deploying an expandable stent within the helical anchor such that, upon expansion, one or more leaflets of the cardiac valve are trapped between the expandable stent and the first turn of the helical anchor;

wherein a replacement valve body is disposed within the expandable stent;

wherein the helical anchor limits expansion of the expandable stent;

wherein a portion of the helical anchor that passes through the opening defined by the valve leaflets of the cardiac valve is positioned at a first commissural region between the valve leaflets; and wherein an outer edge of the first commissural region extends radially beyond the portion of the helical anchor that passes through the opening defined by valve leaflets of the cardiac valve after the expandable stent is deployed.

6. A method of repairing a cardiac valve of a heart, comprising:

inserting a first turn of a helical anchor through an opening defined by valve leaflets of the cardiac valve, such that the first turn is deployed in a ventricle of the heart, wherein the first turn engages a ventricular side of the cardiac valve;

deploying a second turn of the helical anchor in an atrium of the heart;

deploying an expandable stent within the helical anchor such that, upon expansion, one or more leaflets of the cardiac valve are trapped between the expandable stent and the first turn of the helical anchor;

wherein a replacement valve body is disposed within the expandable stent;

wherein the helical anchor limits expansion of the expandable stent; and wherein an inner diameter of the helical anchor is smaller than a greatest width of the opening defined by valve leaflets of the cardiac valve.

7. A method of repairing a cardiac valve of a heart, comprising:

inserting a first turn of a helical anchor through an opening defined by valve leaflets of the cardiac valve, such that the first turn is deployed in a ventricle of the heart, wherein the deployed first turn engages a ventricular side of the cardiac valve;

deploying a second turn of the helical anchor in an atrium of the heart;

deploying an expandable stent within the helical anchor such that, upon expansion, one or more leaflets of the cardiac valve are trapped between the expandable stent and the first turn of the helical anchor;

wherein a replacement valve body is disposed within the expandable stent;

wherein the helical anchor limits expansion of the expandable stent; and wherein the deployed first turn of the helical anchor has a diameter that is smaller than a major axis of the cardiac valve.

8. A method of repairing a cardiac valve of a heart, comprising:

inserting a first turn of a helical anchor through an opening defined by valve leaflets of the cardiac valve, such that the first turn is deployed in a ventricle of the heart, wherein the first turn engages a ventricular side of the cardiac valve;

deploying a second turn of the helical anchor in an atrium of the heart;

deploying an expandable stent within the helical anchor such that, upon expansion, one or more leaflets of the cardiac valve are trapped between the expandable stent and the first turn of the helical anchor;

wherein a replacement valve body is disposed within the expandable stent;

wherein the helical anchor limits expansion of the expandable stent; and reshaping an annulus of the cardiac valve using the helical anchor causing a minor axis of the cardiac valve to increase in length and causing a major axis of the cardiac valve to decrease in length.

9. A method of repairing a cardiac valve of a heart, comprising:

inserting a first turn of a helical anchor through an opening defined by valve leaflets of the cardiac valve, such that the first turn is deployed in a ventricle of the heart, wherein the first turn engages a ventricular side of the cardiac valve;

deploying a second turn of the helical anchor in an atrium of the heart;

deploying an expandable stent within the helical anchor such that, upon expansion, one or more leaflets of the cardiac valve are trapped between the expandable stent and the first turn of the helical anchor;

wherein a replacement valve body is disposed within the expandable stent;

wherein the helical anchor limits expansion of the expandable stent; and wherein the expandable stent, when implanted, does not contact an entire circumference of a valve annulus of the cardiac valve of the heart.

* * * * *